United States Patent
Helletzgruber et al.

(10) Patent No.: US 10,923,219 B2
(45) Date of Patent: *Feb. 16, 2021

(54) METHOD TO ASSIGN WORD CLASS INFORMATION

(71) Applicant: Nuance Communications, Inc., Burlington, MA (US)

(72) Inventors: Matthias Helletzgruber, Vienna (AT); Kresimir Rajic, Vienna (AT)

(73) Assignee: Nuance Communications, Inc., Burlington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/716,990

(22) Filed: Dec. 17, 2019

(65) Prior Publication Data

US 2020/0202992 A1 Jun. 25, 2020

Related U.S. Application Data

(63) Continuation of application No. 15/991,861, filed on May 29, 2018, now Pat. No. 10,515,719, which is a
(Continued)

(30) Foreign Application Priority Data

Nov. 28, 2002 (EP) .................... 02102656

(51) Int. Cl.
*G16H 15/00* (2018.01)
*G06F 40/20* (2020.01)
(Continued)

(52) U.S. Cl.
CPC ............ *G16H 15/00* (2018.01); *G06F 40/20* (2020.01); *G06F 40/268* (2020.01);
(Continued)

(58) Field of Classification Search
CPC .... G06F 40/205; G06F 40/211; G06F 40/268; G06F 40/279; G06F 40/284;
(Continued)

(56) References Cited

U.S. PATENT DOCUMENTS

| 4,860,899 A | 8/1989 | McKee |
| 4,914,590 A | 4/1990 | Loatman et al. |

(Continued)

FOREIGN PATENT DOCUMENTS

| DE | 19533541 C1 | 3/1997 |
| JP | 2001-075968 | 3/2001 |
| JP | 2002-297632 | 10/2002 |
| WO | WO 98/19253 A1 | 5/1998 |

OTHER PUBLICATIONS

Yi Su, Fang Zheng, and Yinfei Huang, "Design of a Semantic Parser with Support to Ellipsis Resolution in a Chinese Spoken Language Dialogue System", Sep. 3-7, 2001, Eurospeech 2001 7th European Conference on Speech Communication and Technology 2nd Interspeech Event (Year: 2001).*

(Continued)

*Primary Examiner* — Eric Yen
(74) *Attorney, Agent, or Firm* — Wolf, Greenfield & Sacks, P.C.

(57) ABSTRACT

An assignment device (1) assigns word class information (WKI) to one or more words of text information (ETI). Based on word-class sequence information (WK-AI) formed from this assigned word class information (WKI), actions (A) are executed in order to notify the user of conflicts or to provide the user with background information (HI) relating to words in the text information (TT).

33 Claims, 1 Drawing Sheet

Related U.S. Application Data continuation of application No. 14/596,900, filed on Jan. 14, 2015, now Pat. No. 9,996,675, which is a continuation of application No. 14/079,069, filed on Nov. 13, 2013, now Pat. No. 8,965,753, which is a continuation of application No. 13/236,835, filed on Sep. 20, 2011, now Pat. No. 8,612,209, which is a continuation of application No. 10/536,239, filed as application No. PCT/IB03/04963 on Oct. 31, 2003, now Pat. No. 8,032,358.

(51) Int. Cl.
| | | |
|---|---|---|
| *G06F 40/30* | (2020.01) | |
| *G06F 40/40* | (2020.01) | |
| *G06F 40/268* | (2020.01) | |
| *G06F 40/284* | (2020.01) | |
| *G06F 40/289* | (2020.01) | |
| *G16H 20/10* | (2018.01) | |
| *G10L 15/26* | (2006.01) | |

(52) U.S. Cl.
CPC .......... *G06F 40/284* (2020.01); *G06F 40/289* (2020.01); *G06F 40/30* (2020.01); *G06F 40/40* (2020.01); *G16H 20/10* (2018.01); *G10L 15/26* (2013.01)

(58) Field of Classification Search
CPC ........ G06F 40/289; G06F 40/30; G06F 40/35; G06F 40/20; G06F 40/40; G16H 15/00; G16H 20/10; G10L 15/26
See application file for complete search history.

(56) References Cited

U.S. PATENT DOCUMENTS

| | | | |
|---|---|---|---|
| 4,930,077 A | | 5/1990 | Fan |
| 4,994,966 A | | 2/1991 | Hutchins |
| 5,146,406 A | | 9/1992 | Jensen |
| 5,384,831 A | | 1/1995 | Creswell et al. |
| 5,384,893 A | | 1/1995 | Hutchins |
| 5,477,451 A | | 12/1995 | Brown et al. |
| 5,508,912 A | | 4/1996 | Schneiderman |
| 5,594,638 A | * | 1/1997 | Iliff .................. G06Q 40/12 705/3 |
| 5,625,748 A | | 4/1997 | McDonough et al. |
| 5,627,914 A | | 5/1997 | Pagallo |
| 5,664,109 A | | 9/1997 | Johnson et al. |
| 5,671,426 A | | 9/1997 | Armstrong, III |
| 5,721,938 A | | 2/1998 | Stuckey |
| 5,761,631 A | | 6/1998 | Nasukawa |
| 5,772,635 A | | 6/1998 | Dastur et al. |
| 5,794,177 A | * | 8/1998 | Carus .................. G06F 40/268 704/9 |
| 5,802,495 A | | 9/1998 | Goltra |
| 5,836,771 A | | 11/1998 | Ho et al. |
| 5,860,059 A | | 1/1999 | Aust et al. |
| 5,887,120 A | | 3/1999 | Wical |
| 5,891,178 A | | 4/1999 | Mann et al. |
| 5,930,746 A | | 7/1999 | Ting |
| 5,933,822 A | | 8/1999 | Braden-Harder et al. |
| 5,943,669 A | | 8/1999 | Numata |
| 6,026,410 A | | 2/2000 | Allen et al. |
| 6,055,494 A | * | 4/2000 | Friedman ............ G06F 40/289 704/9 |
| 6,058,366 A | | 5/2000 | Tarkiainen et al. |
| 6,070,761 A | | 6/2000 | Bloom et al. |
| 6,076,051 A | * | 6/2000 | Messerly ............. G06F 40/30 704/9 |
| 6,085,162 A | | 7/2000 | Cherny |
| 6,104,989 A | | 8/2000 | Kanevsky et al. |
| 6,122,613 A | | 9/2000 | Baker |
| 6,122,615 A | | 9/2000 | Yamamoto |
| 6,173,261 B1 | | 1/2001 | Arai et al. |
| 6,182,028 B1 | | 1/2001 | Karaali et al. |
| 6,223,150 B1 | | 4/2001 | Duan et al. |
| 6,233,561 B1 | | 5/2001 | Junqua et al. |
| 6,243,669 B1 | | 6/2001 | Horiguchi et al. |
| 6,278,968 B1 | | 8/2001 | Franz et al. |
| 6,282,507 B1 | | 8/2001 | Horiguchi et al. |
| 6,304,848 B1 | | 10/2001 | Singer |
| 6,308,158 B1 | | 10/2001 | Kuhnen et al. |
| 6,330,529 B1 | | 12/2001 | Ito |
| 6,356,865 B1 | | 3/2002 | Franz et al. |
| 6,374,224 B1 | | 4/2002 | Horiguchi et al. |
| 6,434,524 B1 | | 8/2002 | Weber |
| 6,442,522 B1 | | 8/2002 | Carberry et al. |
| 6,442,524 B1 | | 8/2002 | Ecker et al. |
| 6,450,956 B1 | | 9/2002 | Rappaport et al. |
| 6,501,937 B1 | | 12/2002 | Ho et al. |
| 6,516,321 B1 | | 2/2003 | De La Huerga |
| 6,523,172 B1 | | 2/2003 | Martinez-Guerra et al. |
| 6,526,629 B1 | | 3/2003 | Warner et al. |
| 6,529,902 B1 | | 3/2003 | Kanevsky et al. |
| 6,772,120 B1 | | 8/2004 | Moreno et al. |
| 6,788,767 B2 | | 9/2004 | Lambke |
| 6,915,254 B1 | * | 7/2005 | Heinze ................. G16H 50/20 704/9 |
| 6,934,675 B2 | | 8/2005 | Glinski et al. |
| 6,963,831 B1 | | 11/2005 | Epstein |
| 6,983,239 B1 | | 1/2006 | Epstein |
| 6,985,852 B2 | | 1/2006 | Wang |
| 6,999,933 B2 | | 2/2006 | Hoi |
| 7,016,828 B1 | * | 3/2006 | Coyne ................. G06F 40/106 704/9 |
| 7,027,975 B1 | | 4/2006 | Pazandak et al. |
| 7,031,908 B1 | | 4/2006 | Huang et al. |
| 7,080,013 B2 | | 7/2006 | Fellenstein et al. |
| 7,289,825 B2 | | 10/2007 | Fors et al. |
| 7,333,966 B2 | | 2/2008 | Dozier |
| 7,379,946 B2 | | 5/2008 | Carus et al. |
| 7,493,253 B1 | | 2/2009 | Ceusters et al. |
| 7,536,637 B1 | | 5/2009 | Nauerz et al. |
| 7,548,859 B2 | | 6/2009 | Thompson et al. |
| 7,603,269 B2 | | 10/2009 | Kaneko et al. |
| 7,610,192 B1 | | 10/2009 | Jamieson |
| 7,853,445 B2 | | 12/2010 | Bachenko et al. |
| 7,917,363 B2 | | 3/2011 | Starkie |
| 8,032,358 B2 | | 10/2011 | Helletzgruber et al. |
| 8,117,034 B2 | | 2/2012 | Gschwendtner |
| 8,612,209 B2 | | 12/2013 | Helletzgruber et al. |
| 8,694,335 B2 | | 4/2014 | Yegnanarayanan |
| 8,738,403 B2 | | 5/2014 | Flanagan et al. |
| 8,965,753 B2 | | 2/2015 | Helletzgruber et al. |
| 9,564,126 B2 | | 2/2017 | Ganong, III et al. |
| 9,818,398 B2 | | 11/2017 | Ganong, III et al. |
| 9,996,675 B2 | | 6/2018 | Helletzgruber et al. |
| 10,515,719 B2 | | 12/2019 | Helletzgruber et al. |
| 2001/0051881 A1 | | 12/2001 | Filler |
| 2002/0004803 A1 | | 1/2002 | Serebrennikov |
| 2002/0029157 A1 | | 3/2002 | Marchosky |
| 2002/0052748 A1 | * | 5/2002 | Portilla ............... G06F 40/55 704/270 |
| 2002/0057203 A1 | | 5/2002 | Borders et al. |
| 2002/0062227 A1 | * | 5/2002 | Yuyama ............... G16H 15/00 705/3 |
| 2002/0091509 A1 | * | 7/2002 | Zoarez ................. G06F 40/279 704/6 |
| 2002/0107690 A1 | | 8/2002 | Souvignier |
| 2002/0188452 A1 | * | 12/2002 | Howes ................. G06F 40/174 704/270 |
| 2003/0009331 A1 | | 1/2003 | Schalkwyk et al. |
| 2003/0028367 A1 | | 2/2003 | Chalabi |
| 2003/0105638 A1 | | 6/2003 | Taira |
| 2003/0115083 A1 | | 6/2003 | Masarie et al. |
| 2003/0167189 A1 | * | 9/2003 | Lutgen ................. G06F 19/326 705/3 |
| 2003/0208352 A1 | | 11/2003 | Lee |
| 2003/0208465 A1 | | 11/2003 | Yurko et al. |
| 2003/0217335 A1 | | 11/2003 | Chung et al. |
| 2003/0233224 A1 | * | 12/2003 | Marchisio ............ G06F 40/35 704/4 |

(56) References Cited

U.S. PATENT DOCUMENTS

| | | |
|---|---|---|
| 2003/0233251 A1 | 12/2003 | Haskell et al. |
| 2004/0002872 A1 | 1/2004 | Wright |
| 2004/0030540 A1 | 2/2004 | Ovil et al. |
| 2004/0088158 A1 | 5/2004 | Sheu et al. |
| 2004/0158455 A1 | 8/2004 | Spivack et al. |
| 2004/0172305 A1* | 9/2004 | Soerensen ............... G06Q 50/24 705/3 |
| 2004/0220797 A1 | 11/2004 | Wang et al. |
| 2005/0108001 A1* | 5/2005 | Aarskog ............... G06F 40/289 704/10 |
| 2005/0114140 A1 | 5/2005 | Brackett et al. |
| 2006/0041428 A1 | 2/2006 | Fritisch et al. |
| 2007/0106508 A1 | 5/2007 | Khan et al. |
| 2007/0260977 A1 | 11/2007 | Allard et al. |
| 2007/0299651 A1 | 12/2007 | Koll et al. |
| 2008/0228769 A1 | 9/2008 | Lita et al. |
| 2010/0049756 A1 | 2/2010 | Chemitiganti et al. |
| 2010/0094657 A1 | 4/2010 | Stern et al. |
| 2010/0114597 A1 | 5/2010 | Shreiber et al. |
| 2010/0324927 A1 | 12/2010 | Tinsley |
| 2010/0324936 A1 | 12/2010 | Vishnubhatla et al. |
| 2011/0202332 A1* | 8/2011 | Abir ........................ G06F 40/55 704/4 |
| 2012/0010875 A1 | 1/2012 | Helletzgruber et al. |
| 2012/0166225 A1 | 6/2012 | Albro et al. |
| 2014/0067380 A1 | 3/2014 | Helletzgruber et al. |
| 2015/0127374 A1 | 5/2015 | Helletzgruber et al. |
| 2019/0139634 A1 | 5/2019 | Helletzgruber et al. |

OTHER PUBLICATIONS

S. Wermter, G. Arevian, "Modular preference Moore machines in news mining agents", Jul. 25-28, 2001, IEEE, Proceedings Joint 9th IFSA World Congress and 20th NAFIPS International Conference, pp. 1792-1797 (Year: 2001).*

EP 03758567.6, Sep. 27, 2010, Office Action.

EP 12187525.6, Oct. 29, 2012, European Search Report.

EP 12187526.4, Oct. 25, 2012, European Search Report.

Office Action for European Patent Application No. 03 758 567.6 dated Sep. 27, 2010.

European Search Report for European Application No. 12187525.6 dated Oct. 29, 2012.

European Search Report for European Application No. 12187526.4 dated Oct. 25, 2012.

Chang et al., Non-Clinical Errors Using Voice Recognition Dictation Software for Radiology Reports: A Retrospective Audit. J Digit Imaging. 2011;24:724-8.

Cooper et al., Chapter 9. Orchestration and Flow. About Face 2.0—The Essentials of Interaction Design. 2003. 43 pages.

Duda et al., Chapter 1. Introduction. Pattern Classification. 2001. 2d Eds. 32 pages.

Norman, The Design of Everyday Things. Basic Books. 1988. pp. 99-101, 177-179, 197-200.

Voll, A Methodology of Error Detection: Improving Speech Recognition in Radiology. Thesis Submitted in Partial Fulfillment of the Requirements for the Degree of Doctor of Philosophy. Simon Fraser University. Spring 2006. 208 pages.

* cited by examiner

METHOD TO ASSIGN WORD CLASS INFORMATION

This Application is a Continuation of U.S. Application Ser. No. 15/991,861, filed May 29, 2018, entitled "METHOD TO ASSIGN WORD CLASS INFORMATION", which is a Continuation of U.S. Application Ser. No. 14/596,900, filed Jan. 14, 2015, entitled "METHOD TO ASSIGN WORD CLASS INFORMATION", which is a Continuation of U.S. Application Ser. No. 14/079,069, filed Nov. 13, 2013, entitled "METHOD TO ASSIGN WORD CLASS INFORMATION", which is a Continuation of U.S. Application Ser. No. 13/236,835, filed Sep. 20, 2011, entitled "CLASSIFYING TEXT VIA TOPICAL ANALYSIS, FOR APPLICATIONS TO SPEECH RECOGNITION", which is a Continuation of U.S. Application Ser. No. 10/536,239, filed May 24, 2005, entitled "CLASSIFYING TEXT VIA TOPICAL ANALYSIS, FOR APPLICATIONS TO SPEECH RECOGNITION", which is a national stage filing under 35 U.S.C. 371 of International Patent Application Serial No. PCT/IB2003/004963, filed Oct. 31, 2003, entitled "METHOD TO ASSIGN WORD CLASS INFORMATION". Foreign priority benefits are claimed under 35 U.S.C. § 119(a)-(d) or 35 U.S.C. § 365(b) of European application number 02102656.2, filed Nov. 28, 2002.

The invention relates to an assignment device with assignment means for assigning supplementary information to one or more words in the text information.

The invention further relates to an assignment method for assigning supplementary information to one or more words of text information.

The invention further relates to a computer program product, which can be loaded directly into the internal memory of a digital computer and which comprises sections of software code.

An assignment device of this kind, an assignment method of this kind and a computer program product of this kind are known from document U.S. Pat. No. 6,434,524. This document discloses a computer to which a microphone is connected and which implements voice recognition software. A user of this known computer can speak an item of speech information, which may contain words of text information or command information, into the microphone, whereupon the computer establishes a recognized text information. Assignment means of the computer search for certain words in the recognized text information and select an associated command context in order to recognize command information in the recognized text information.

The user may, for instance, speak the speech information "What time is it" into the microphone in order to obtain information about the current time from the computer. If the computer's voice recognition software is operating correctly, the computer recognizes firstly the recognized text information "What time is it". The assignment means compare the words of the recognized text information with key words stored in a command-context memory, and assign the recognized text information to the command context "time" since the key word "time" was found in the recognized text information.

The command context "time" stipulates that the sequence of words "What time" has to be found in the recognized text information in order to recognize the command information for inquiring as to the current time. On recognizing a certain sequence of words in the command information hereby recognized, action means of the known computer activate an action in which the current time is established and, by means of "text to speech" means, is spoken so as to be acoustically audible to the user.

In the case of the known assignment device and the known assignment method, the disadvantage has arisen that the user has to speak precisely the correct words in the correct order in order that the desired action is implemented by the computer.

It is an object of the invention to create an assignment device of the generic type specified in the first paragraph, an assignment method of the generic type specified in the second paragraph and a computer program product of the generic type specified in the third paragraph, in all of which the above-mentioned disadvantage is avoided. To achieve the above-mentioned object, in an assignment device of this kind, the assignment means are designed to assign word class information to one or more words of text information, and to deliver word-class sequence information containing the assigned word-class information, and linkage means designed to detect the presence of at least two specific items of word-class information in the word-class sequence information and to deliver the corresponding linkage information are provided, and action means designed to activate an action when specific linkage information or a specific combination of linkage information is delivered by the linkage means are provided.

To achieve the above-mentioned object, in an assignment method of this kind, the following procedural steps are provided:

Assignment of word-class information to one or more words of text information;

Delivery of word-class sequence information containing the assigned word-class information;

Detection of the presence of at least two specific items of word-class information in the word-class sequence information;

Delivery of linkage information identifying the detected word-class information;

Activation of an action when specific linkage information or a specific combination of linkage information is delivered.

To achieve the above-mentioned object, in a computer program product of this kind, the steps of the assignment method in accordance with the invention are implemented with the computer when the product is running on the computer.

As a result of the features in accordance with the invention, it is achieved that the assignment device assigns individual, some or all words of the recognized text information to word-class information and inserts these into word-class sequence information. Word-class information identifies a word class to which the particular word or the particular word sequence is to be assigned. For instance, the names of medicaments—such as "Aspirin", "Ospen" and "Sanostol"—can be assigned to a word class "medicament".

Linkage means now search for the presence of specific word-class information in the word-class sequence information, and deliver linkage information if specific combinations of specific items of word-class information have been found in the word-class sequence information. The action means check, directly after the delivery of one or more or all items of linkage information of the text information, or at any subsequent moment, whether specific linkage information or specific combinations of linkage information have been delivered. If linkage information or combinations of linkage information of this kind have been detected by the action means, the action means will activate the action defined for this purpose.

This gives rise to the advantage that, through the presence of specific combinations of word classes, a statement can be made concerning the content of the text information, and specific actions can be automatically initiated accordingly. For example, in the case of the presence of the word class "medicament" (for the word Ospen in the text information) and the word class "allergy" (for the word Penicillin allergy in the text information) in a medical report, the linkage means could output the corresponding linkage information, which is used to activate the following action. The computer establishes the components of the medicament from the background dictionary and checks whether the patient is allergic to a component of the medicament. A warning notice for the doctor can then be actioned if applicable.

The measures as claimed in claims 2 and 10 give rise to the advantage that only the presence of specific word-class information within a maximum word-class distance (e.g. three words, one sentence or a paragraph of text information; five adjacent items of word-class information in the word-class sequence information . . . ) is checked. As a result, an even more unambiguous statement concerning the contents of the text information is possible. Actions can therefore be executed with significantly more success.

The measures as claimed in claim 3 give rise to the advantage that an assignment device that is especially easily realized in practice is obtained.

The measures as claimed in claims 4 and 11 give rise to the advantage that words of text information can be assigned to word-class information even in the course of the implementation of the voice recognition method by a voice recognition device. Information that is available during the implementation of the voice recognition method can hereby also be used for the assignment of the word-class information by the assignment means, which enables an even greater reliability of the word-class sequence information, the linkage information and the actions derived therefrom.

The measures as claimed in claims 5 and 12 give rise to the advantage that the attention of a user can be drawn to a particular situation by the action means.

The measures as claimed in claim 6 give rise to the advantage that the user can set the action means manually in order to have the actions he wishes executed as the result of the occurrence of sequences of word-class information in the word-class sequence information as defined by the user.

The measures as claimed in claims 7 and 14 give rise to the advantage that the action means automatically establish background information (e.g. instruction text) for words of specific word classes (e.g. medicament) from a background dictionary. This background information may either be displayed against the word during dictation or at any subsequent moment.

The invention will be further described with reference to examples of embodiments shown in the drawing, to which, however, the invention is not restricted.

Figure 1:
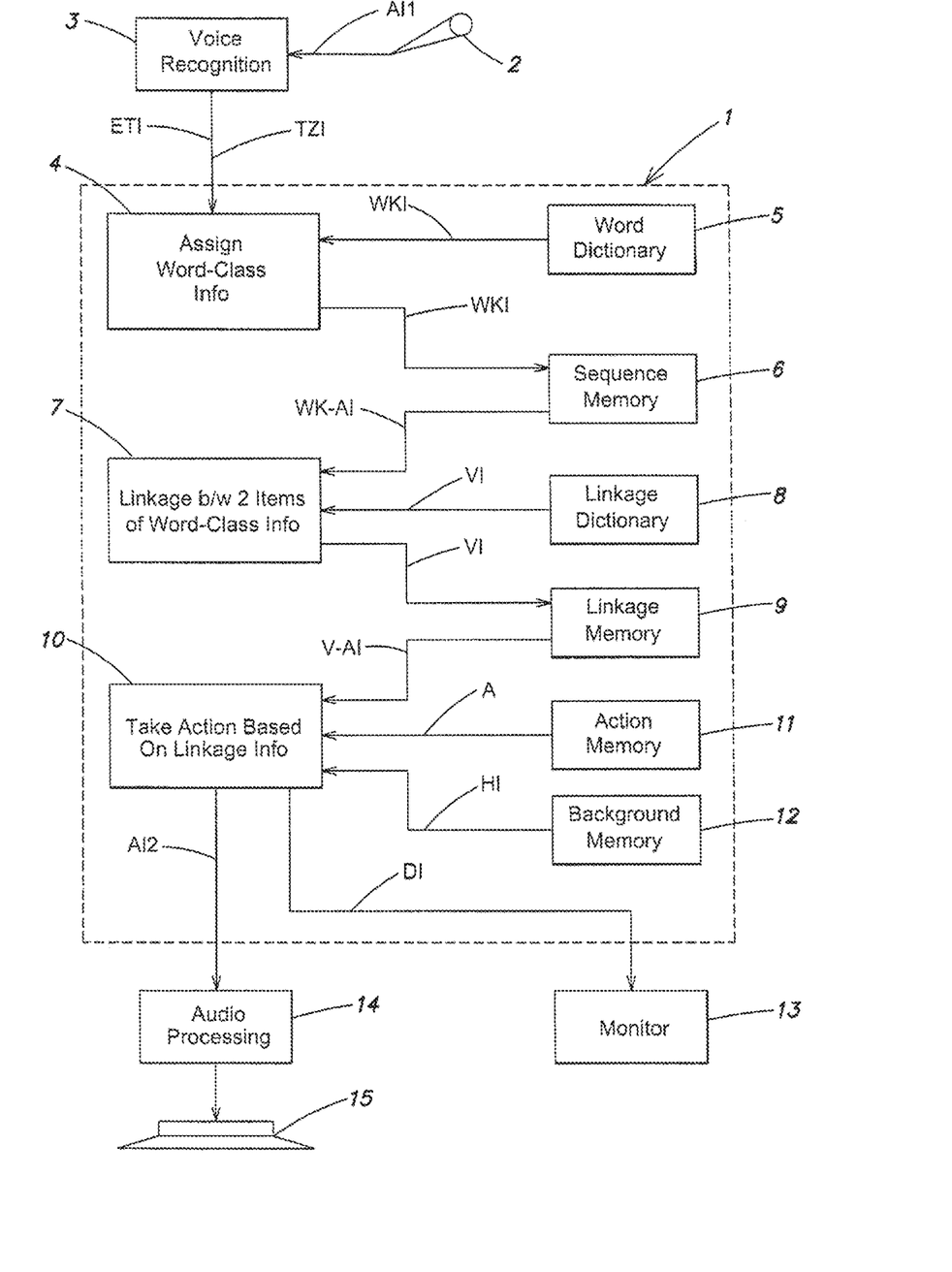
FIG. 1 shows a block circuit diagram of an assignment device for assigning word-class information and for executing actions.

FIG. 1 shows a block circuit diagram of an assignment device 1 for assigning word-class information WKI to word information WI of text information TI and for executing actions A. A microphone 2 is connected to a voice recognition device 3 and is designed to deliver a first acoustic information AI1 to voice recognition device 3. Voice recognition device 3 takes the form of a computer, which implements voice recognition software, as known from the Philips voice recognition software FreeSpeech™ for example. A user can speak a text into microphone 2, and voice recognition device 3 implements a voice recognition method and, following this, delivers recognized text information ETI and supplementary text information TZI to assignment device 1. Assignment device 1 hereby also takes the form of a computer, which implements assignment software in accordance with an assignment method. It is especially advantageous if a computer implements both the voice recognition software and the assignment software.

The supplementary text information TZI is information that voice recognition device 3 has established during the implementation of the voice recognition method for recognizing the recognized text information ETI. For example, supplementary text information TZI may comprise the information that the recognized text information ETI should be assigned to the specialist area of radiology, or comprises specialist legal terminology. Supplementary text information TZI may further identify multiple successive words of the recognized text information ETI as a typical phrase (e.g. the United States of America).

The assignment device 1 is equipped with assignment means 4, which is designed to assign word-class information WKI as supplementary information to one or more words of the recognized text information ETI. To this end, assignment means 4 is designed to search for the word information. WI for the words of the recognized text information ETI in a word dictionary memory 5. For each word information WI of a word stored in word dictionary memory 5, an item of word-class information WKI assigned to this word information WI is stored in assignment. Table 1 shows a small part of the word information WI stored in word dictionary memory 5, together with assigned word-class information WKI. Any other form of assigned storage is also possible.

TABLE 1

| WI | WKI | |
| --- | --- | --- |
| Aspirin | Medicament | WKI-1 |
| Canale Grande | Sightseeing | WKI-2 |
| Railway | Transportation | WKI-3 |
| Ospen | Medicament | WKI-1 |
| Venice | City | WKI-4 |

The assignment means 4 is designed to evaluate the supplementary text information TZI in order to enable a better assignment of word-class information WKI or a faster search for the associated word-class information WKI. For example, based on the supplementary text information TZI that the recognized text information ETI is a text from the specialist area of radiology, assignment means 4 could start the search for words of recognized text information ETI in a section of word dictionary memory 5 in which specialist radiology terminology is stored. Similarly, the words "Canale Grande" would be recognized as a word sequence to which just one word-class information WKI is then assigned.

When the assignment means 4 has found a word or a word sequence in word dictionary memory 5, assignment means 4 reads the assigned word-class information WKI and stores it in a sequence memory 6 of assignment device 1. Assignment means 4 thereby assigns to the sequence of words of recognized text information ETI a sequence of associated word-class information WKI, which is stored as word-class sequence information WK-AI in sequence memory 6.

The assignment device 1 is further equipped with linkage means 7, which is designed to detect the presence of at least two specific items of word-class information WKI in word-class sequence information WK-AI and to deliver corresponding linkage information VI. In particular, linkage means 7 is designed to deliver the corresponding linkage information VI only if the presence of at least two items of word-class information WKI is detected within a maximum word-class distance WEE. To this end, linkage means 7 compares the word-class information WKI contained in word-class sequence information WK-AI within the maximum word-class distance WEE with combinations of word-class information WKI stored in a linkage dictionary memory 8.

TABLE 2

| WK1 | VI |
|---|---|
| WKI-1 + WKI-17 | VI-1 |
| WKI-4 + WKI-6 + WKI-28 | VI-2 |
| WKI-4 + WKI-7 | VI-3 |

Table 2 shows a small part of the combinations of word-class information WKI stored in linkage dictionary memory 8, wherein linkage information VI is stored in assignment to each such combination.

For example, WEE=5 could be stipulated as the maximum word-class distance and word-class sequence information WK-AI=. . . WKI-3/WKI-36/WKI-1/WKI-5/WKI-6/WKI-17/WKI-49. . . could be stored for a recognized item of text information ETI in sequence memory 6. In this case, linkage means 7 would examine the five items of word-class information WKI contained both before and after each item of word-class information WKI in the word-class sequence information WK-AI as to whether a combination stored in linkage dictionary memory 8 can be detected. Linkage means 7 would hereby detect the combination of word-class information WKI-1 and WKI-17 within the specified word-class distance WEE and deliver the linkage information VI-1. The order of occurrence of word-class information WKI in word-class sequence information WK-AI is generally not significant. It therefore makes no difference whether WK-AI=. . . WKI-1/ . . . /WKI-A17/ . . . or WK-AI=. . . WKI-17/ . . . WKI-A1. With some combinations of items of word-class information WKI, however, a specific order may have been stipulated in linkage dictionary memory 8.

The stipulation of the maximum word-class distance WEE gives rise to the advantage that a certain connection exists in terms of content. Linkage information VI is therefore delivered only if words in the direct vicinity have been assigned corresponding word-class information WKI. This advantage is explained in greater detail below with reference to two application examples. Word-class distance WEE could also identify the number of words, sentences or paragraphs in the recognized text information ETI in the vicinity of which the combination of word-class information WKI stored in linkage dictionary memory 8 is to be sought, around the particular word-class information WKI to be examined.

The linkage means 7 is designed to store the established linkage information VI in a linkage memory 9. Assignment device 1 is further equipped with action means 10, which is designed to activate an action when a specific item of linkage information VI or a specific sequence of linkage information VI has been delivered by linkage means 7 and stored in linkage memory 9. To this end, action means 10 reads the linkage information VI stored in linkage memory 9 as linkage sequence information V-AI, and searches in an action memory 11 for the linkage information VI or specific sequences of linkage information VI contained in linkage sequence information V-AI. If the linkage information VI or specific sequence of linkage information VI sought is found in action memory 11, action means 10 reads the associated stored action information A from action memory 11. The read action information A is then executed or at least activated by action means 10.

TABLE 3

| VI | A |
|---|---|
| VI-1 | A-1 |
| VI-1 + VI-3 | A-2 |
| VI-3 | A-3 |

Table 3 shows a small part of the linkage information VI stored in action memory 11 and the action information A stored in association. For example, if linkage information VI-3 is contained in linkage sequence information V-AI, action A-3 could be executed. Action A-3 could, for example, take the form of searching a background memory 12 for background information HI relating to the particular words to which word-class information WKI-4+WKI-7 and, ultimately, linkage information VI-3 have been assigned. The read background information HI could be processed by action means 10 and reproduced visually on a monitor 13 as display information DI. Similarly, the read background information HI could be delivered to audio processing means 14 as second acoustic information AI2, and reproduced acoustically from a loudspeaker 15.

Below, a first embodiment of assignment device 1 is explained in detail, wherein it is assumed that a doctor is dictating a medical report into microphone 2. The doctor dictates ". . . a sensitivity to milk products . . . the patient reported a Penicillin allergy, which must be checked out. The patient . . . and Ospen was prescribed, to be taken 3 times daily . . . Aspirin was also prescribed, for the patient to take as required in the event of further attacks of pain."

The voice recognition means 3 recognizes a recognized text information ETI corresponding to this dictation, and delivers this to assignment means 4 together with the supplementary text information that the recognized text information ETI is to be assigned to the field of medicine. Assignment means 4 searches in word dictionary memory 5 for the word information WI contained in the recognized text information ETI, and stores the following word-class sequence information WK-AI in sequence memory 6. To facilitate understanding, the word contained in the recognized text information ETI/the word stored in word dictionary memory 5 and the associated word-class information WKI are given in each case: WKI-AI=". . . sensitivity→Allergy→WKI-28/milk products→Active agent group → WKI-322/ . . . /→patient→Patient→WKI-27/Penicillin→Active agent→WKI-444/Allergy→Allergy→WKI-28/Ospen→Medicament→WKI-342/prescribed→Prescription→WKI-99/3 times→Quantity→WKI-77/daily→Periodicity→WKI-88/ . . . /Aspirin→Medicament→WKI-342/prescribed→Prescription→WKI-99/Patient →Patient→WKI-27/as required→Periodicity→WKI-88. . . "

Assignment means 4 is advantageously designed to establish the particular wordstem form for each word of recognized text information. ETI before searching for word information WI in word dictionary memory 5, and to search for this in word dictionary memory 5. Assignment means 4 may hereby have established for the word "milk products" in the recognized text information ETI the wordstem form "milk product" and searched for this singular form in word dictionary memory 5. As a result, the number of words to be stored in word dictionary memory 5 can be significantly reduced, meaning that memory space can be saved.

In accordance with the application example, a word-class distance WEE=4 has been assumed. Linkage means 7 then checks whether, contained within four items of word-class information WKI-322/WKI-27/WKI-444/WKI-28 surrounding the first word-class information WKI-28 in the stored word-class sequence information WK-AI, is an item of word class information WKI stored as a combination in linkage dictionary memory 8.

In accordance with the application example, it is assumed that the following is stored in linkage dictionary memory 8: WKI-28 (Allergy)+WKI-322 (Active agent group) →VI-17. It is further assumed that the following is stored in action memory 11: VI-17A-55 (visual warning). Action means 10 then delivers to monitor 13 the text information TI="Warning: allergic to milk products" as display information DI. This warning may be displayed in its own window adjacent to the recognized text on monitor 13. This gives rise to the advantage that the doctor or any other person who has to process the medical report receives important information from the medical report without having to read it all in detail.

In accordance with the application example, it is further assumed that the following is stored in linkage dictionary memory 8: WKI-444 (Active agent)+WKI-28 (Allergy)→18. It is further assumed that the following is stored in action memory 11: VI-18→A-54 (Active agent group established for active agent)+A-55 (visual warning). Action means 10 then establishes from background memory 12 to which active agent group the active agent "Penicillin" belongs and then delivers text information TI="Warning: allergic to Penicillin-type active agents" to monitor 13 as display information DI. This gives rise to the advantage that the doctor does not have to look for the active agent group to which the patient is allergic in a medical dictionary, and furthermore, the doctor receives an appropriate warning.

It may be mentioned that, as a result of the implementation of action A-54 to establish the active agent group for the active agent, linkage information VI-17 (WKI-28 (Allergy)+WKI-322 (Active agent group) can be inserted into linkage sequence information V-AI against the active agent. This linkage information VI-17 could consequently give rise to a further action A with the following linkage information VI in linkage sequence information V-AI. This gives rise to the advantage that linkage sequence information V-AI is dynamically expanded and adjusted to improve the result.

In accordance with the application example, it is further assumed that the following is stored in linkage dictionary memory 8: WKI-342 (Medicament)+WKI-99 (Prescription)→VI-42. It is further assumed that the following is stored in action memory 11: VI-42→A-66 (printout of a prescription)+A-78 (check whether there is a conflict between allergy and active agent of medicament). To implement action A-66, the action means stores the medicament "Ospen" and subsequently the medicament "Aspirin" in a buffer store in order that, at the end of the implementation of all actions A relating to the recognized text information ETI, a prescription is printed for the patient, with which he can purchase the medicaments from a pharmacy. To implement action A-78, action means 10 establishes, via an Internet connection to a central medicament database not shown in FIG. 1, the active agents in the medicaments Ospen and Aspirin, and compares these with the patient's allergies. From this examination it is established that an active agent (Anoxicillin) of these medicaments is assignable to the "Penicillin-type" active agent group. A visual warning is then shown on monitor 13 and, because of the risk, an acoustic warning is also given from loudspeaker 15. This gives rise to the great advantage that assignment device 1 relieves the doctor of a significant amount of work and, like a doctor's assistant, makes him aware of dangerous active agent combinations.

An action A-103 could also be assigned to linkage information VI-42 and action means 10 would then search background memory 12 for a medicament that is comparable with the one prescribed, but significantly cheaper. This could produce significant savings in the medical field.

It may be mentioned that a user can continuously adjust assignment device 1 in line with his requirements. The user can both add new word information items and word-class information items WKI to word dictionary memory 5, and also add new combinations of word-class information WKI and linkage information VI to the linkage dictionary memory and new linkage information VI and associated actions A to the action memory 11. Information already stored can be amended according to the user's wishes. This gives rise to the advantage that assignment device 1 can always be better adjusted by the user and, as a result, can relieve the user of more and more work.

It may be mentioned that warnings or supplementary information established by action means 10 may also be displayed in relation to a word from the recognized text ETI in the following manner. Each word of the recognized text information ETI to which supplementary information has been assigned is shown specially marked on monitor 13. For example, such words could be underlined or a lower case "i" could be displayed at the end of the particular word. To retrieve the supplementary information, the user can activate the word or the "i" with the computer mouse and the cursor, whereupon the supplementary information relating to this word is shown in a small window.

In accordance with a second embodiment, it is assumed that a user of a computer on which a commercially available word processing program is being implemented is writing the following letter: "Dear Sandra, I am traveling today by train to Venice and will meet tomorrow at Canal Grande", Assignment means 4 stores the following word-class sequence information WK-AI in sequence memory 6: WKI-AI=". . . Sandra→Name→WKI-90/traveling→Journey→WKI-777/today→Timing→WKI-32/train→Transportation→WKI-80/to→Direction→WKI-65/ Venice→City→WKI-767/tomorrow→Timing→WKI-32/ Canale Grande→Sightseeing→WKI-2.

In accordance with the second application example, it is further assumed that the following is stored in linkage dictionary memory 8: WKI-777 (Journey)+WKI-32 (Timing)+WKI-80 (Transportation)+WKI-767 (City=Destination)→VI-64. It is further assumed that the following is stored in action memory 11: VI-64→A-60 (search at www.fahrplan.com). To implement action 60, action means 10 connects in a manner not shown in FIG. 1 with the Internet server having the address www.fahrplan.com establishes possible train connections for the user and displays these on monitor 13. Also stored against word-class information WKI-2 (Sightseeing) is linkage information VI-55 and against this the action A-70 (established background information on sightseeing). To implement the action A-70, action means 10 searches in background dictionary 12 and under www.sehenswürdigkeiten.com for background information HI on Canale Grande, and displays this on monitor 13 or announces it acoustically from loudspeaker 15.

This gives rise to the advantage that the assignment device is constantly active in the background by way of assistance to the user, and adds appropriate information and warnings to the content of text information TI.

It may be mentioned that multiple items of word-class information WKI may be assigned to one word in word dictionary memory 5. For example, word-class information WKI-767 (City) and word-class information WKI-2 (Sightseeing) could be assigned to the word "Venice". Depending on the combinations of word-class information items WKI stored in linkage dictionary memory 8, the city of Venice will be evaluated as a destination, or background information HI relating to Venice for sightseeing will be established.

It may be mentioned that the assignment device in accordance with the invention may be used in combination with many different word-processing computer programs. For example, the assignment device could analyze all mail that can be received by an email program, and subject it to preliminary processing before the user reads it. When he reads his emails, the user will already have available a large amount of supplementary information established by the assignment device.

It may be mentioned that, before the assignment by the assignment device, a cluster analysis can be undertaken of a part of the text (e.g. a sentence, paragraph . . . ) of the recognized text information in order to implement specific word class assignments of higher priority. A certain weighting of the linkage information takes place hereby.

The invention claimed is:

1. A method comprising:
   analyzing text relating to medical treatment of a patient to identify one or more concepts expressed in the text, wherein the analyzing of the text comprises acts of:
   mapping at least some words and/or phrases included in the text to a plurality of corresponding classes, one or more of the plurality of corresponding classes each indicating a category of information of a plurality of categories of information to which a corresponding word and/or phrase included in the text relates;
   mapping at least some of the plurality of corresponding classes to one or more particular combinations of corresponding classes, wherein the mapping of the at least some of the plurality of corresponding classes to the one or more particular combinations comprises determining whether any of a plurality of combinations of corresponding classes appears in the at least some of the plurality of corresponding classes;
   determining a distance between corresponding classes mapped to the one or more particular combinations of corresponding classes; and
   identifying one or more concepts expressed in the text based at least in part on the determined distance between corresponding classes mapped to the one or more particular combinations of corresponding classes.

2. The method of claim 1, wherein the text comprises a report regarding an encounter between a clinician and the patient.

3. The method of claim 1, comprising performing at least one action in response to identifying the one or more concepts.

4. The method of claim 3, wherein the at least one action relates to delivering information relating to at least one of the words and/or phrases mapped to the plurality of corresponding classes.

5. The method of claim 4, wherein the delivered information is retrieved from at least one storage device accessible via the Internet.

6. The method of claim 3, wherein:
   at least one of the words and/or phrases mapped to the plurality of corresponding classes relates to an allergy of the patient toward an active agent belonging to an active agent group; and
   the at least one action comprises providing a warning of an allergy by the patient to active agents in the active agent group.

7. The method of claim 3, wherein:
   the words and/or phrases mapped to the plurality of corresponding classes comprise a first word and/or phrase and a second word and/or phrase;
   the first word and/or phrase identifies a medicament and the second word and/or phrase relates to an allergy concerning the patient;
   the at least one action comprises providing a warning that the patient may be allergic to the medicament.

8. The method of claim 3, wherein:
   at least one of the words and/or phrases mapped to the plurality of corresponding classes identifies a medicament; and
   the at least one action comprises generating a prescription for the patient for the medicament.

9. The method of claim 8, wherein generating the prescription comprises initiating printing a paper copy of the prescription for the patient.

10. The method of claim 3, wherein:
    at least one of the words and/or phrases mapped to the plurality of corresponding classes identifies a particular medicament; and
    the at least one action comprises searching for a different medicament that is comparable to the particular medicament.

11. The method of claim 1, wherein the text is produced by a voice recognition component.

12. The method of claim 11, comprising operating the voice recognition component to produce the text.

13. The method of claim 1, wherein determining a distance between corresponding classes comprises determining whether the corresponding classes appear within a predetermined distance of one another in the text.

14. The method of claim 13, wherein the predetermined distance is defined in relation to a specific combination of corresponding classes to which the at least some of the plurality of corresponding classes is mapped.

15. The method of claim 13, wherein the predetermined distance relates to a number of words in the text separating a first word or phrase of the words and/or phrases mapped to the plurality of corresponding classes and a second word or phrase of the words and/or phrases mapped to the plurality of corresponding classes.

16. The method of claim 1, wherein:
    information is employed in the mapping of the at least some words and/or phrases to the plurality of corresponding classes, the mapping of the at least some of the plurality of corresponding classes to the one or more particular combinations of corresponding classes, and/or the determining of a distance between the corresponding classes mapped to the one or more particular combinations of corresponding classes; and
    the information is editable by a user.

17. A device, comprising:
at least one computer, programmed to analyze text relating to medical treatment of a patient to identify one or more concepts expressed in the text, wherein the analyzing of the text comprises:
mapping at least some words and/or phrases included in the text to a plurality of corresponding classes, one or more of the plurality of corresponding classes each indicating a category of information of a plurality of categories of information to which a corresponding word and/or phrase included in the text relates;
mapping at least some of the plurality of corresponding classes to one or more particular combinations of corresponding classes, wherein the mapping of the at least some of the plurality of corresponding classes to the one or more particular combinations comprises determining whether any of a plurality of combinations of corresponding classes appears in the at least some of the plurality of corresponding classes;
determining a distance between corresponding classes mapped to the one or more particular combinations of corresponding classes; and
identifying one or more concepts expressed in the text based at least in part on the determined distance between corresponding classes mapped to the one or more particular combinations of corresponding classes.

18. The device of claim 17, wherein the at least one computer is programmed to analyze text comprising a report regarding an encounter between a clinician and the patient.

19. The device of claim 17, wherein the at least one computer is programmed to perform at least one action in response to identifying the one or more concepts.

20. The device of claim 19, wherein the at least one action relates to delivering information relating to at least one of the words and/or phrases mapped to the plurality of corresponding classes.

21. The device of claim 20, wherein the delivered information is retrieved from at least one storage device accessible via the Internet.

22. The device of claim 19, wherein:
at least one of the words and/or phrases mapped to the plurality of corresponding classes relates to an allergy of the patient toward an active agent belonging to an active agent group; and
the at least one action comprises providing a warning of an allergy by the patient to active agents in the active agent group.

23. The device of claim 19, wherein:
the words and/or phrases mapped to the plurality of corresponding classes comprise a first word and/or phrase and a second word and/or phrase;
the first word and/or phrase identifies a medicament and the second word and/or phrase relates to an allergy concerning the patient;
the at least one action comprises providing a warning that the patient may be allergic to the medicament.

24. The device of claim 19, wherein:
at least one of the words and/or phrases mapped to the plurality of corresponding classes identifies a medicament; and
the at least one action comprises generating a prescription for the patient for the medicament.

25. The device of claim 24, wherein generating the prescription comprises initiating printing a paper copy of the prescription for the patient.

26. The device of claim 19, wherein:
at least one of the words and/or phrases mapped to the plurality of corresponding classes identifies a particular medicament; and
the at least one action comprises searching for a different medicament that is comparable to the particular medicament.

27. The device of claim 17, wherein the at least one computer is programmed to analyze text produced by a voice recognition component.

28. The device of claim 27, wherein the at least one computer is programmed to operate the voice recognition component to produce the text.

29. The device of claim 17, wherein the at least one computer is programmed to determine a distance between corresponding classes at least in part by determining whether the corresponding classes appear within a predetermined distance of one another in the text.

30. The device of claim 29, wherein the predetermined distance is defined in relation to a specific combination of corresponding classes to which the at least some of the plurality of corresponding classes is mapped.

31. The device of claim 29, wherein the predetermined distance relates to a number of words in the text separating a first word or phrase of the words and/or phrases mapped to the plurality of corresponding classes and a second word or phrase of the words and/or phrases mapped to the plurality of corresponding classes.

32. The device of claim 17, comprising at least one memory storing information employed in the mapping of the at least some words and/or phrases to the plurality of corresponding classes, the mapping of the at least some of the plurality of corresponding classes to the one or more particular combinations of corresponding classes, and/or the determining of a distance between the corresponding classes mapped to the one or more particular combinations of corresponding classes; and
wherein the at least one computer is programmed to enable a user to edit the information.

33. At least one non-transitory computer-readable medium storing instructions which, when executed by at least one computer, cause the at least one computer to perform a method comprising:
analyzing text relating to medical treatment of a patient to identify one or more concepts expressed in the text, wherein the analyzing of the text comprises acts of:
mapping at least some words and/or phrases included in the text to a plurality of corresponding classes, one or more of the plurality of corresponding classes each indicating a category of information of a plurality of categories of information to which a corresponding word and/or phrase included in the text relates;
mapping at least some of the plurality of corresponding classes to one or more particular combinations of corresponding classes, wherein the mapping of the at least some of the plurality of corresponding classes to the one or more particular combinations comprises determining whether any of a plurality of combinations of corresponding classes appears in the at least some of the plurality of corresponding classes;
determining a distance between corresponding classes mapped to the one or more particular combinations of corresponding classes; and identifying one or more concepts expressed in the text based at least in part on the determined distance between corresponding classes mapped to the one or more particular combinations of corresponding classes.

\* \* \* \* \*